(12) United States Patent
Curphey

(10) Patent No.: US 7,012,148 B2
(45) Date of Patent: Mar. 14, 2006

(54) COMPOSITIONS AND METHODS FOR THIONATION DURING CHEMICAL SYNTHESIS REACTIONS

(75) Inventor: Thomas J. Curphey, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 324 days.

(21) Appl. No.: 10/344,014

(22) PCT Filed: Sep. 25, 2001

(86) PCT No.: PCT/US01/29937

§ 371 (c)(1),
(2), (4) Date: May 9, 2003

(87) PCT Pub. No.: WO02/26909

PCT Pub. Date: Apr. 4, 2002

(65) Prior Publication Data

US 2003/0176714 A1    Sep. 18, 2003

(51) Int. Cl.
*C07D 339/04* (2006.01)
*C07D 339/02* (2006.01)
*C07D 339/00* (2006.01)

(52) U.S. Cl. ............. 549/35; 549/36; 514/441; 252/182.3; 252/182.12

(58) Field of Classification Search ........... 252/182.11, 252/182.13, 182.3, 182.35; 514/441; 549/35, 549/36
See application file for complete search history.

(56) References Cited

U.S. PATENT DOCUMENTS

| | | | | | |
|---|---|---|---|---|---|
| 2,553,586 | A | * | 5/1951 | Bartleson et al. | 508/348 |
| 2,613,205 | A | * | 10/1952 | Hill | 564/15 |
| 2,742,430 | A | * | 4/1956 | McBride, Jr. | 508/355 |
| 3,294,712 | A | * | 12/1966 | Clark et al. | 521/106 |
| 3,522,179 | A | * | 7/1970 | Le Suer | 508/486 |
| 3,791,789 | A | | 2/1974 | Alink | 21/2.5 R |
| 4,240,821 | A | | 12/1980 | Rasheed et al. | 71/90 |
| 4,370,343 | A | * | 1/1983 | Mohrbacher et al. | 514/430 |
| 5,401,470 | A | | 3/1995 | Poli | 422/96 |
| 5,739,228 | A | | 4/1998 | Meijs et al. | 526/209 |
| 5,750,560 | A | | 5/1998 | Christen et al. | 514/441 |

FOREIGN PATENT DOCUMENTS

| | | |
|---|---|---|
| EP | 0 275 651 A1 | 7/1987 |
| JP | 02981196 A | 9/1988 |
| JP | 06009392 A | 1/1994 |

* cited by examiner

*Primary Examiner*—Joseph D. Anthony
(74) *Attorney, Agent, or Firm*—Licata & Tyrrell P.C.

(57) ABSTRACT

Compositions and methods for using these compositions to produce high yields of thionated compounds are provided.

7 Claims, No Drawings

COMPOSITIONS AND METHODS FOR THIONATION DURING CHEMICAL SYNTHESIS REACTIONS

INTRODUCTION

This invention was supported in part by funds from the U.S. government (NIH Grant No. CA39416 and NSF Grant No. CHE-9904454) and the U.S. government may therefore have certain rights in the invention.

BACKGROUND OF THE INVENTION

Thionoesters and related thionolactones, $R_1CSOR_2$, are versatile intermediates for organic synthesis (Jones, B. A. and Bradshaw, J. S. 1984 Chem Rev. 84:17–30). For example, they may be transformed into ethers, $R_1CH_2OR_2$, by reduction with Raney nickel (Baxter, S. L. and Bradshaw, J. S. 1981 J. Org. Chem. 46:831–832; Bradshaw et al. 1983 J. Org. Chem. 48:1127–1129) or tin hydrides (Smith et al. 1988 Phosphorus Sulfur 37:257–260; Jang et al. 1999 Tetrahedron 55:3479–3488) and into difluoroethers, $R_1CF_2OR_2$, by treatment with (diethylamino)sulfur trifluoride (Bunnelle et al. 1990 J. Org. Chem. 55:768–770). Reaction of thionolactones with organometallic agents, $R_3M$, leads to tetrahedral intermediates with may be trapped with methyl iodide and then reduced stereoselectively to alkylated cyclic ethers, $R_1R_3CHOR_2$, a sequence which has proven valuable in the preparation of complex polyether natural products (Nicolaou et al. 1990 J. Am. Chem. Soc. 112:6263–6276; Nicolaou et al. 1995 J. Am. Chem. Soc. 1995 117:10227–10238). Of the possible precursors to thionoesters, the corresponding esters are highly attractive starting materials, being readily available commercially or by a variety of synthetic methods. However, the ester carbonyl group is one of the most difficult of the common carbonyl derivatives to thionate.

For example, the apparently straight-forward synthesis of thionoesters from esters using $P_4S_{10}$ suffers from generally low yields (Jones, B. A. and Bradshaw, J. S. 1984 Chem. Rev. 84:17–30). Replacing $P_4S_{10}$ with 2,4-(bis(4-methoxyphenyl)-1,3,2,4-dithiadiphosphetane-2,4-disulfide (Lawesson's reagent, LR) results in improved yields of thionoesters and thionolactones, making these derivatives much more accessible and attractive as synthetic intermediates (Pederson et al. 1978 Bull. Soc. Chim. Belg. 87:293–297; Scheibye et al. 1979 Tetrahedron 35:1339–1343). However, the high equivalent weight of LR and the need to use a full mole of the reagent per mol of ester (Pederson et al. 1978 Bull. Soc. Chim. Belg. 87:293–297) means that the thionoester often comprises a small percent by weight of the crude reaction mixture. Because the reagent-derived byproducts cannot be removed by any extractive procedure, the total reaction mixture must be subjected to chromatography, and the method becomes impractical and expensive for large scale preparations. Moreover, chromatographic separation of the desired product from LR byproducts may, in some cases, be difficult or impossible.

Accordingly, there is a need for higher yield methods for production of thionoesters and thionolactones as these compounds are useful in a variety of technologies.

For example, the dithiolethiones (3H-1,2-dithiole-3-thiones) are a class of chemopreventive agents which display marked activity against a variety of animal models of cancer (Kensler, T. W. et al. 1994. ACS Sympos. Ser. 546: 154–163). The basic structure of this class of compounds is shown below as Formula I.

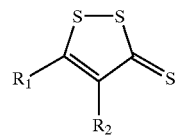

In fact, one representative of this class of heterocyclic sulfur compounds, known as oltipraz ($R_1$=pyrazinyl, $R_2$=methyl), is currently undergoing human trials in an area of China where there is a high incidence of liver cancer (Wang, J. et al. 1999. J. Natl. Cancer Inst. 91:347–354). In order to exploit the therapeutic potential of this compound and others that are chemically similar, methods of synthesis are needed that are both efficient (i.e., high yield) and cost-effective (i.e., require minimal post-reaction purification).

Unfortunately, the existing methods for synthesis of this sulfur-containing ring system are not optimum (Pedersen, C. T. 1982. Adv. Heterocycl. Chem. 31:63–113), especially for production and preparation of the large quantities of material that are needed for biological testing in animals, including humans. Current methods for synthesis of dithiolethiones employ reaction of a 3-oxoester with a mixture of $P_4S_{10}$ and sulfur. The reaction is generally conducted in boiling toluene or xylene (Schmidt, U. et al. 1960. Justus Liebigs Ann. Chem. 631:129–139; Lozach, N. and L. Legrand. 1952. C. R. Seances Acad. Sci. 234:1291–1293). However, the yields with this method are seldom above 50% and are typically low, in the range of 0 to 20% (Schmidt, U. et al. 1960. Justus Liebigs Ann. Chem. 631:129–139).

Replacing the $P_4S_{10}$ with LR, while resulting in higher yield of dithiolethiones, is still not practical for large scale preparations due to high cost and difficulty in separating the dithiolethiones from other byproducts.

Other attempts to improve the procedures for synthesis of the dithiolethione ring include treatment of 3-oxo dithioic acids with either a solution of polysulfanes in liquid hydrogen sulfide containing hydrogen bromide (Curphey, T. J. and H. H. Joyner. 1993. Tetrahedron Lett. 34:3703–3706) or with a combination of hexamethyldisilathiane and N-chlorosuccinimide in the presence of imidazole (Curphey, T. J. and H. H. Joyner. 1993. Tetrahedron Lett. 34:7231–7234). These synthetic procedures have also resulted in only limited success.

SUMMARY OF THE INVENTION

An object of the present invention is to provide a composition for thionation of compounds which comprises a phosphorus sulfide and a siloxane. In one embodiment the phosphorus sulfide comprises $P_4S_{10}$ (phosphorus pentasulfide, tetraphosphorus decasulfide) and the siloxane is hexamethyldisiloxane.

Another object of the present invention is to provide methods for producing thionated compounds which comprises treating a compound to be thionated with a reagent comprising a phosphorus sulfide and a siloxane. Exemplary thionated compounds which can be produced via these methods include, but are not limited to, chemopreventive dithiolethiones, the tuberculostatic drug ethionamide and the sedative-hypnotic thiobarbital.

Accordingly, another object of the present invention is to provide methods for synthesis of these therapeutic agents by treating an ester or lactone with a reagent comprising a phosphorus sulfide and a siloxane. In a preferred embodiment, the synthetic method is used to produce the chemopreventive agent 3H-1,2-dithiole-3-thione by treating a 3-oxoester with a reagent comprising a phosphorus sulfide and a siloxane. Also provided in the present invention are therapeutic agents produced in accordance with this synthetic method.

DETAILED DESCRIPTION OF THE INVENTION

A new reagent for thionation of compounds during chemical synthesis reactions has been identified. The reagent was produced by addition of a siloxane compound to a phosphorus sulfide mixture. In one embodiment the siloxane used was hexamethyldisiloxane (HMDO). However, other siloxanes such as hexaethylsiloxane can also the used. The siloxane is mixed with a phosphorus sulfide containing mixture such as the $P_4S_{10}$ sulfur mixture as depicted in equation 1.

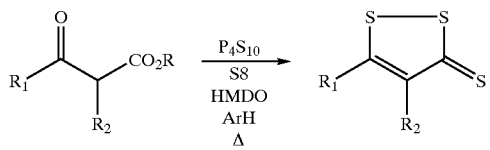

Use of this reagent for thionation of 3-oxoesters significantly increased the yield of the dithiolethione over existing methods and simplified the production of the final product. Therefore, the composition of the present invention provides a reagent that can be used in the preparation of large quantities, known as large scale production, of thionated compounds.

Also provided in the present invention is a method for production of thionated compounds by treatment during chemical synthesis reactions with this reagent. The methods of the present invention are particularly useful in the large scale production of thionated compounds. Further, these methods have the advantage that reagent-derived byproducts may be removed by a simple hydrolytic workup or by filtration through silica gel, rather than by chromatography, as required by Lawesson's reagent.

The method of the present invention for production of a thionated compound is exemplified below in equation 2.

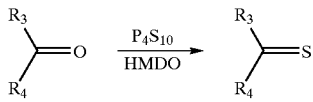

In this equation, $R_3$ and $R_4$ may be any alkyl group, aryl group, heterocyclic group, or heteroatom such as S, O, N, or Si. Addition of HMDO to the $P_4S_{10}$ sulfur mixture of equation 1 greatly increased the yield of dithiolethione. Using the production of 5-methyl-3H-1,2-dithiole-3-thione from ethyl acetoacetate as a model, as shown in equation 3, the method of the present invention was shown to be a high yield thionation procedure.

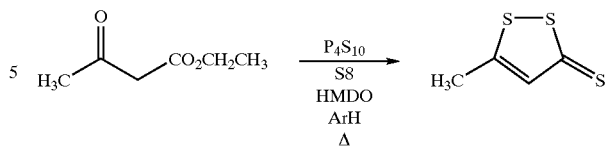

It was determined that 0.6 moles of $P_4S_{10}$ per mole of 3-oxoester was optimum. Addition of elemental sulfur up to 1 gram atom per mole of 3-oxoester had a beneficial effect on yield, as had been found for Lawesson's reagent (Pederson, B.S. and S.O. Lawesson. 1978. *Tetrahedron* 35:2433–2437) and for $P_4S_{10}$ alone (Schmidt, U. et al. 1960. *Justus Liebigs Ann. Chem.* 631:129–139). However, more than 1 gram atom of elemental sulfur per mole had no effect. By direct gas chromatography (GC) analysis of the reaction mixture it was established that 2 to 2.5 moles of HMDO per mole of 3-oxoester were consumed. Xylene was used for these experiments, although the reaction has been successfully performed using toluene, ethyl benzene, chlorobenzene, HMDO, dioxane, and 1,1,2,2-tetrachloroethane.

The method of the present invention involved refluxing a xylene solution of the 3-oxoester with 0.6 moles of $P_4S_{10}$, 1 gram atom of sulfur and 3 moles of HMDO per mole of 3-oxoester until high performance liquid chromatography (HPLC) analysis showed that the reaction was complete. Results obtained using representative 3-oxoesters are shown in Table 1. In all but two cases, trials 6 and 11, the chromatographic yields were quite high. Some evidence of a steric effect was apparent, with dithiolethiones with bulky alkyl groups, such as trials 4 and 5, requiring significantly longer reaction times. Except for trials 5 and 6, isolation of the pure dithiolethiones did not require chromatography, in contrast to prior methods. The phosphorus-containing byproducts formed during the reactions were easily removed during further purification by exposure to aqueous $K_2CO_3$, which hydrolyzed the compounds to water soluble derivatives. After removing small amounts of dark-colored polar materials by filtration through a short plug of silica gel plus activated carbon, the final product was purified by distillation, sublimation and/or recrystallization.

A direct comparison was made of the method of the present invention for thionation and dithiolethione synthesis with the method employing Lawesson's reagent. Trials were performed using six 3-oxoester substrates (trials 1, 3, 4, 8, 9 and 11 in Table 1). In all trials examined, the method of the present invention was more effective than the use of Lawesson's reagent. One trial where the method of the present invention did not offer any advantage over the use of $P_4S_{10}$ alone was in synthesis of oltipraz, trial 11, where the yield obtained with $P_4S_{10}$ was not improved by the addition of HMDO.

GC analysis of the product formed from reaction of $P_4S_{10}$ with HMDO, with or without the presence of sulfur, revealed that these components do not react in the absence of the 3-oxoester, ruling out the possibility that modification of $P_4S_{10}$ by HMDO occurs prior to interaction with the substrate.

TABLE 1

Preparation of 3H-1, 2-dithiole-3-thiones from 3-oxoesters, $P_4S_{10}$ and Hexamethyldisiloxane

| | $R_1$-Group[a] | $R_2$-Group[b] | Time (hr)[c] | Yields (%) HPLC[d] | Isolated[e] | LR[f] |
|---|---|---|---|---|---|---|
| 1 | Me | H | 1 | 98 | 80 | 84 |
| 2 | Et | H | 2 | 98 | 74 | |
| 3 | Ph | H | 1 | 83 | 70 | 80 |
| 4 | t-Butyl | H | 8 | 93 | 83 | 79 |
| 5[7] | 1-Adamantyl | H | 5 | 78 | 70 | |
| 6[8] | ferrocenyl | H | 0.5 | 45 | 36 | |
| 7 | Me | Me | 2 | 95 | 87 | |
| 8 | Me | I—Pr | 2 | 86 | 72 | 80 |
| 9 | —(CH$_2$)$_4$— | | 1 | 98 | 86 | 73 |
| 10 | —(CH$_2$)$_3$— | | 2 | 83 | 71 | |
| 11 | pyrazinyl | Me | 1 | 19 | — | 2.5 |

[a]Chemical identity of the $R_1$-group for the reactant shown in equation 2.
[b]Chemical identity of the $R_2$-group for the reactant shown in equation 2.
[c]Reaction time in refluxing xylene.
[d]Yield determined by HPLC using the external standard for each compound as a method of comparison for yield determination.
[e]Yield of distilled or recrystallized material. Physical properties such as boiling or melting points were in good agreement with known values for each compound tested.
[f]Maximum HPLC yield obtained with Lawesson's reagent, as a way to validate the improved efficiency of the method of the present invention.
[7]Represents a new compound: $C_{13}H_{16}S_3$
[8]Represents a new compound: $C_{13}H_{10}FeS_3$ Data of Table 1 demonstrate that the combination of $P_4S_{10}$, sulfur and HMDO provide a highly effective reagent for converting 3-oxoesters to dithiolethiones.

High yield, lost cost production of dithiolethiones via the reagents and methods of the present invention provides the means necessary for exploitation of the therapeutic potential of these compounds. Accordingly, a preferred aspect of the present invention relates to use of the composition and method in the production of a thionated chemopreventive age. For example, a 3-oxoester can be treated with a phosphorus sulfide compound and a siloxane compound in accordance with the present invention to produce a thionated chemopreventive agent such as a 3H-1,2-dithiole-3-thione. Chemopreventive agents produced via the methods and compositions of the present invention are obtained at a lower cost of production and at a higher, more easily purified yield.

Examples of other compounds which can be produced by these methods are the tuberculostatic drug ethionamide (Liebermann, D. et al. 1958 *Bull Soc. Chim. Fr.* 687) and the sedative-hypnotic thiobarbital (Zima, O, and VonWerder, F. 1951 U.S. Pat. No. 2,561,689).

The compositions and methods of the present invention are also useful in transforming simple esters and lactones to their thiono derivatives. An exemplary reaction wherein the phosphorus sulfide $P_4S_{10}$ and the siloxane HMDO are used to produce ethyl thionobenzoate from ethyl benzoate is depicted in equation 4 ($R_1$=Ph, $R_2$=Et).

In these experiments, it was demonstrated that the combination of $P_4S_{10}$ and HMDO in refluxing xylene produced the corresponding thionoester in good yield, as determined by high performance liquid chromatography (HPLC) analysis of the reaction mixture. This series of experiment established that 0.25 to 0.33 moles of $P_4S_{10}$ per mole of ester were required to obtain maximum yields of the thionoester and that approximately 1 mole of HMDO was consumed in the process. Using standard conditions of 0.25 to 0.33 moles of $P_4S_{10}$ and 1.7 moles of HMDO per mole of ester, thionation of a series of esters and lactones was examined and compared with thionation by LR under similar conditions. The carbonyl substrates were chosen to reflect a variety of structural types including aromatic esters, aliphatic esters, phenolic esters, and unsaturated esters, as well as small ring, medium ring and macrocyclic lactones. Also included were substrates whose thionation by LR was reported to be problematic. Results from these experiments are depicted in Table 2.

TABLE 2

Thionation of esters and lactones ($R_1CO_2R_2$) by $P_4S_{10}$/HMDO and Lawesson's reagent (LR)[a]

| | $R_1$ | $R_2$ | Sol.[b] | Chrom. Yields[c] (%) $P_4S_{10}$/HMDO | LR | Isolated Yields[d] (%) |
|---|---|---|---|---|---|---|
| 1 | Ph | Et | A, A | 81 | 81 | 73 |
| 2 | Ph | Me | A, A | 92 | 92 | 79 |
| 3 | Ph | I—Pr | A, A | 95 | 92 | 83 |
| 4 | n-Hexyl | Et | A, A | 87 | 76 | 75 |
| 5 | Me | 2-Napthyl | B, B[e] | 41 | 40 | 30 |
| 6 | 1-Naphthyl | Et | A, A | 91 | 83 | 87 |
| 7 | 4-Nitrophenyl | Me | A, A | 28 | 4 | 21 |
| 8 | PhCH=CH— | Et | C, C | 75 | 70 | 72 |
| 9 | Ph$_2$C=C(CN)— | Et | A, A | 51 | 59 | 42 |
| 10 | —CH(CH$_3$)CH$_2$CH$_2$— | | D, C | 87 | 85 | 78 |
| 11 | —(CH$_2$)$_4$— | | D, C | 82 | 69 | 65 |
| 12 | —(CH$_2$)$_5$— | | D, C | 82 | 73 | 77 |
| 13 | —(CH$_2$)$_6$— | | D, C | 77 | 58 | 62 |
| 14 | —(CH$_2$)$_{15}$— | | A, A | 87 | 84 | 86 |

[a]Standard reaction conditions for determination of chromatographic yields: 3 mmol ester, 0.75 mmol $P_4S_{10}$ or 3.6 mmol LR, 5 mmol HMDO (if used), and 3 ml dry solvent were refluxed under argon until HPLC showed the yield of thionoester to have reached a maximum. This required between 45 minutes and 30 hours. For entries 1, 2 and 9, the amount of $P_4S_{10}$ was increased to 1 mmol, which gave slightly improved yields.
[b]The first letter is the reaction solvent used for the P4S10/HMDO reagent and the second letter is the reaction solvent used for LR; A = xylenes, B = ethyl benzene, C = toluene, D = acetonitrile.
[c]Maximum yield of distilled or recrystallized material obtained using the $P_4S_{10}$/HMDO reagent.
[d]Yield of distilled or recrystallized material obtained using the $P_4S_{10}$/HMDO reagent. These experiments were carried out on a 3–50 mmol scale. Physical properties, $^1$H-NMR spectra, and $^{13}$C-NMR spectra of the isolated thionoesters were in good agreement with literature values. Purities, as determined by GC and HPLC, were greater than 97% in all cases.
[e]Ethyl benzene was used as the reaction solvent because of overlap between xylenes and the thionoester product in HPLC chromatograms.

As shown in Table 2, chromatographic yields of thionoesters and thionolactones using the method of the present invention were equal to or greater than those obtained with LR for 13 out of 14 cases examined. In only one case, entry 9, was a slightly low yield obtained with the method of the present invention. Further, as shown in entry 7, the method of the present invention can be used to produce thionoesters from agents such as methyl 4-nitrobenzoate which were previously reported not to produce a thionoester with LR (Baxter, S. L. and Bradshaw, J. S. 1981 J. Org. Chem. 46:831–832). As indicated by Table 2, a thionoester product is actually produced by LR, but the amount is too small to be useful. In contrast, using a composition and method of the present invention, a thionoester could be readily isolated by silica gel chromatography at a relatively useful yield.

For simple esters and for the one macrocyclic lactone examined (entry 14), refluxing xylene as solvent proved to be the most generally useful reaction conditions. However, the much greater reactivity of small and medium ring lactones (entries 10 through 13) permitted a wider range of solvents and conditions to be employed, of which acetonitrile at reflux proved to be especially effective. Using this solvent, it was even possible to convert caprolactone to the corresponding thionolactone at room temperature, the reactions with the reagent of the present invention reaching 65% chromatographic yield in 8 hours and a maximum yield of 70% in 20 hours. In contrast, the corresponding reaction with LR required 1 hour in refluxing toluene to reach a similar maximum yield (entry 12).

Thionation of δ-valerolactone (entry 11) is also demonstrative of the utility of the method and reagent of the present invention. While Lawesson reported that this lactone failed to give the thiono derivative with LR (Scheibye et al. 1979 Tetrahedron 35:1339–1343), δ-valerolactone does, in fact, undergo thionation by LR in refluxing toluene (entry 11). However, examination of the resulting reaction mixture by thin layer chromatography (TLC) shows comparable amounts of the thionolactone and of a reagent-derived byproduct whose spots exhibited nearly identical $R_f$ values and was extremely problematic to separate. In contrast, the thionolactone from δ-valerolactone produced using a composition and method of the present invention was readily prepared and isolated in 65% yield. Further, the method of the present invention could be routinely scaled up to any desired size.

As expected from experiments described above relating to production of dithiolethiones, mild alkaline hydrolysis of the reagent of the present invention gave a crude product, substantially free of phosphorus-sulfur byproducts, which was readily purified further by distillation or crystallization. Additional purification by silica gel chromatography was only required for entries 7 and 9 of Table 2, primarily to separate unchanged ester from the thionoester product.

It is believed that the reagents and methods of the present invention can also be used in thionation reactions of other classes of compounds including but not limited to thioamides, thioacids, thioketones, thioaldehydes, thioureas, and almost any type of heterocyclic thio compound. In some cases, addition of sulfur to the reagent may not be necessary. One of skill can routinely adapt the methods of the present invention to make and use these other compounds in accordance with the teachings provided herein.

The following non-limiting example is provided to better illustrate the present invention:

EXAMPLES

Example 1

Production of Dithiolethiones

CAUTION: Because of the noxious odor of the product and the liberation of $H_2S$ during the synthesis, all operations should be conducted in a well-ventilated fume hood. A suspension of $P_4S_{10}$ (6.67 g, 15 mmol) and sulfur (0.802 g, 25 mmol) in dry xylene (50 ml) and HMDO (15.9 ml, 75 mmol) was refluxed and stirred mechanically under an atmosphere of dry argon for 5 minutes. Ethyl acetoacetate (3.19 ml, 25 mmol) was added over a 3 minute period and the mixture then refluxed for 1 hour. The resulting red-brown solution was cooled to 0° C. and finely powdered $K_2CO_3$ (8.29 g, 60 mmol) was added, followed by water (10 ml) added dropwise over 30 minutes. (CAUTION: vigorous gas evolution). Acetone (25 ml) was added and the mixture stirred at 0° C. for an additional 90 minutes. The mixture was partitioned between toluene and water, and the organic phase was washed successively with 0.1 M $K_2CO_3$ solution, dilute $Na_2SO_4$ solution, and brine. The extract was dried over anhydrous $Na_2SO_4$ and evaporated in a vacuum. The resulting dark oil was dissolved in toluene, filtered through a short column of silica gel and activated carbon, and the solvent removed in a vacuum. The resulting ruby red oil was recrystallized from $CCl_4$ at −15° C. to give 2.95 g (80% yield) of 5-methyl-3H-1,2-dithiole-3-thione (1, $R^1$=Me, $R^2$=H), as orange crystals, mp 33.5–34.5° C.

Example 2

Production of Isopropyl Thionobenzoate

CAUTION—The reaction and workup should be conducted in a good fume hood. A mixture of isopropyl benzoate (8.13 ml, 50 mmol), $P_4S_{10}$ (7.40 grams, 16.7 mmol), HMDO (17.7 mL, 83.3 mmol), and xylene (50 mL, dried over 3A molecular sieves) was mechanically stirred and refluxed under argon for 8 hours. The reaction mixture was cooled in an ice-bath and treated with aqueous $K_2CO_3$ solution (21 mL of 5.3 M, 111 mmol). Acetone (25 mL) was added and the mixture was stirred vigorously for 30 minutes in the ice-bath. Water and benzene were then added, the layers separated, and the aqueous phase extracted with benzene. The combined organic phase was washed with dilute K2CO3 solution, water and brine, and dried over anhydrous Na2SO4. Evaporation of the solvent and distillation of the residue through a short Vigreaux column gave 7.46 grams (83%) of isopropyl thionobenzoate, bp 54–61° C./0.01 mm:1H NMR $CDCl_3$) δ1.52 (d,J=6.6 Hz, 6H), 5.94(heptuplet, j-6.6 Hz, 1H)), 7.41 (m,2H), 7.55 (m,1H), 8.23 (m,2H); 13C NMR (CDCl3) δ21.32, 75.60, 128.05, 128.85, 132.59, 139.00, 210.68. Analysis by gas chromatography showed 98.3% purity, with 1.5% of the starting ester as the major impurity.

What is claimed is:

1. A method for producing a thionated compound comprising treating the compound to be thionated with a phosphorus sulfide compound and a siloxane compound so that the compound is thionated.

2. The method of claim 1 wherein the compound to be thionated is an ester or lactone.

3. The method of claim 2 wherein the thionated compound produced is a thionoester or a thionolactone.

4. The method of claim 1 wherein the compound to be thionated is a 3-oxoester compound.

5. The method of claim 4 wherein the thionated compound produced is 3H-1,2-dithiole-3-thione.

6. A method for producing a thionated therapeutic agent comprising treating an ester or lactone with a phosphorus sulfide compound and a siloxane compound to produce the thionated therapeutic agent.

7. The method of claim 6 wherein the ester is a 3-oxoester and the thionated therapeutic agent is a chemopreventive agent 3H-1,2dithiole-3-thione.

* * * * *